United States Patent [19]

Goldsberry

[11] Patent Number: Plant 6,626

[45] Date of Patent: Feb. 21, 1989

[54] DWARF CARNATION PLANT 'REDCLOUD'

[75] Inventor: Kenneth L. Goldsberry, Fort Collins, Colo.

[73] Assignee: Colorado State University Research Foundation, Fort Collins, Colo.

[21] Appl. No.: 71,803

[22] Filed: Jul. 10, 1987

[51] Int. Cl.[4] ..... A01H 5/00

[52] U.S. Cl. ..... Plt./73

[58] Field of Search ..... Plt./70–73

*Primary Examiner*—James R. Feyrer

*Attorney, Agent, or Firm*—Edwin L. Spangler, Jr.

[57] ABSTRACT

A carnation plant known by the cultivar name Redcloud was developed through a breeding program and is particularly characterized as to uniqueness by its dwarf growth habit and the following combined characteristics: upon pinching a rooted cutting, forms 3 to 6 lateral stems 22.0 to 26.0 cm long, each developing a terminal flower and 4 to 6 secondary buds which open intermittently after the terminal flowers seneses; red flowers 5.0 to 6.0 cm in diameter with a slight fragrance; can be grown under specified environmental conditions either as a single pinched plant per 10 cm pot or 3 pinched plants per 13 cm pot, which results in an ideal new flowering house plant.

1 Drawing Sheet

My present invention relates to a new and distinct dwarf cultivar of *Dianthus caryophyllus* Linn. identified as plant 85-215-120A and given the name Redcloud.

Redcloud is a product of a breeding program started by me at Colorado State University in 1974, using commercially available semi dwarf germplasm, crossing selected unnamed seedlings and incorporating various known carnation germplasm with an objective of creating dwarf carnation cultivars that could be asexually produced for commercial use, in controlled environments, as flowering house plants.

Redcloud is a sport of 85-215-120 (Quandary) which was originated from a cross made in a controlled breeding program at the Horticulture Department, W. D. Holley Plant Environmental Research Center, Colorado State University, Fort Collins, Colo. using the unnamed seed parent 83-15-20 and an unnamed pollen parent 82-43A, also developed by the present inventor.

Redcloud was discovered and selected as one flowering plant within the progeny of the stated cross by Kenneth L. Goldsberry on Apr. 10, 1986 in a controlled environment in Fort Collins, Colo.

The first act of asexual reproduction of Redcloud was accomplished when vegetative cuttings were taken, by the inventor, from the initial selection in July, 1986 in a controlled environment in Fort Collins, Colo. The initial rooting of the cuttings and performance of the resulting plants have demonstrated that the distinctive characteristics of this new cultivar Redcloud, here in disclosed, appear to be firmly fixed and hold true from generation to generation.

Redcloud has not been observed under all possible environmental conditions. The phenotype may vary significantly with variation in the production environment including irrigation regimes, temperature, light intensity, day length and nutritional programs. It has been observed and evaluated, from a rooted cutting to a mature plant while being grown in Fort Collins and Denver, Colo. and Encintias and Salinas, Calif. under greenhouse conditions, which approximate those generally used in commercial practice.

The following traits, which have been repeatedly observed, characterize Redcloud and distinguishes it as a new and distinct dwarf carnation cultivar:

1. Somatic chromosome is 2n=30
2. A double type flower, similar to commercial cut flower spray types
3. Flower sizes range from 5.0 to 6.0 cm in diameter
4. Watermellon red flower color
5. Medium flowering response on a scale of early, medium or late flowering
6. Three to six lateral shoots develop following a pinch of the main stem
7. The terminal flower, four to six secondary buds and three to six tertiary buds form on each flowering stem. Few or no quaternary buds develop. As the old flowers senese, the secondary buds continue to open, the tertiary buds usually abort
8. Secondary peduncle lengths on a single stem varies between 0.7 to 9 cm
9. Plant height ranges between 22 to 26 cm
10. Little or no fragrance is present There are no dwarf carnation cultivars, for house plant use, presently developed and known to the inventor.

BRIEF DESCRIPTION OF THE DRAWING

The accompanying top colored photograph taken on May 1, 1987, using an 18 percent Kodak photographic gray card as a color base, illustrates in perspective view and the overall appearance of Redcloud (85-215-120A) grown in 10 cm (single plant) and 15 cm (3 plants) azalea pots. The bottom photo shows buds, inflorescence, stem foliage characteristics and color of Redcloud are typical and true as possible with illustrations of this type.

The following detailed description of my new dwarf carnation cultivar are based upon observations of greenhouse grown plants made in 1986 and 1987 at Fort Collins, Colo. The color values were determined in a standard color viewing booth with a 5000° K. fluorescent light source using references developed and published by The Royal Horticultural Society, London, England.

PLANT CHARACTERISTICS

Origin: Sport of seedling selection 85-215-120.

Parentage:

*Seed parent.*—Selected unnamed seedling, 83-15-20 (Goldsberry).

*Pollen parent.*—Selected unnamed seedling 82-43A (Goldsberry).

Classification:

*Botanic.*—*Dianthus caryophyllus* Linn. cv. Redcloud.

*Commercial.*—Dwarf carnation for pot plant production.

Propagation: Vegetative cuttings, 6 to 7 cm. in length initiate visible roots in 8 to 10 days in the winter and 5 to 8 during the summer, when rooted under mist in a rooting medium temperature of 20° C. A quality rooted cutting with an abundance of roots, is usually ready to plant in 15 days in the summer and 18 to 20 in the winter.

Growth habit: Three to four lateral shoots form naturally, but are accelerated by removing the terminal portion of the main stem, at the sixth or seventh node from the top, resulting in a compact, bushy and strong up right plant. Some basal branches may elongate enough to place apical buds on a plane equal to the terminal flowers of the initial stems.

Stems: Numerous lateral branches form close to the base of the plant and vary in length from 22–26 cm, having 5 to 9 nodes with opposite leaves. A reproductive bud usually forms at each upper 6 nodes. Shoots forming at the senveth or tenth node below the terminal flower, usually develop into another flower stem in proper environmental conditions. All stems have a blue-grey glaucous condition, approximating 189B in color.

Foliage: Leaves are abundant and typical of the commercial carnation type. The longest leaves occur at the sixth or seventh node from the top of each stem and range in length from 9.3 to 13.2 cm. The widest leaves occur at nodes four or five and have an average width of 1.0 cm., but are progressively smaller above and below these nodes. Both the upper and lower sides of the leaves are dark green and have a blue-grey glaucous condition. The color of both surfaces is identified as 189B with the surface bloom present and 137A when it is removed.

INFLORESCENCE CHARACTERISTICS

Buds: Terminal buds average 3.0 cm in length just prior to opening and the secondary buds 2.8 to 3.0 cm. The average bud circumference ranges from 4.7 cm for the terminal and secondary buds 4.3 cm, at the first sign of petal color. Significantly visible tertiary buds form on the peduncles of the second through fifth secondary buds, but do not open in low light conditions. Buds are oval in shape and pointed.

Sequence of development: The terminal bud on each stem will show color before any lateral bud color is visible. The opening sequence of the secondary buds is generally at node positions one, three, two and four from the terminal flower position on each stem. In the proper environments, new flower bearing shoots emerge from the seventh to eleventh nodes below the terminal flower and at the base of the plant, creating a perpetual flowering plant in high light conditions.

Flowering response: A rooted cutting pinched 2 to 4 weeks after planting will flower 14 to 16 weeks following the pinch from a October 1 plant date and 11 to 12 weeks from a June 1 date in Fort Collins, Colo. when growing temperatures approximate 11° C. at night and 17° C. during the day.

Inflorescence type: Each initial stem is a semi-compound spray with a terminal bud, 4 to 6 secondary and 4 to 7 tertiary, 1 to 5 quaternary buds and 3 to 5 lateral shoots.

Number of buds and flowers per stem: Each stem has a terminal flower that develops along with the upper most, of the 5 to 8 secondary buds; new flowering shoots usually form at the sixth to ninth nodes of each initial stem resulting in an average of 7.0 flowers per stem. Secondary buds often form in both leaf axils of the first and second nodes. Almost all of the tertiary buds on the fifth, sixth and seventh node position form in both leaf axils. The tertiary and quaternary buds do not develop petals in low light and therefore do not open.

Peduncle length: The length of the peduncles range from 0.7 cm for the top secondary bud to 10.0 cm for the lowest bud, on each stem, when the terminal flower is in prime condition. The peduncles of the tertiary buds vary from 0.2 to 4.5 cm.

Peduncle strength: Strong, holds flowers erect during all growing seasons; degree of brittleness is related to environmental conditions.

Flower:

*Size.*—Terminal flowers range in size from 5.0 to 5.6 cm and the secondaries, 5.0 to 6.0 cm depending on the environment.

*Type.*—Commercial double with 33 to 45 moderately serrated petals in the terminal flowers, which have an average length and width of 4.6 cm and 2.3 cm, respectively.

*Form.*—Sub hemispherical in longitudinal section with the petals adjacent to the calyx, slightly reflexed at maturity. Seldom splits. The secondary flowers are 5.0–6.0 cm in diameter and have average petal lengths of 4.5 cm and 2.5 cm wide. The tertiary buds do not open.

Corolla color: General tonality at a distance of 1 meter: 53C at petal margins. Upper petal surface: newly opened petals are 53C in color, but fade to 54CD in greenhouse conditions. The mid petal color is also 54CD. Lower petal surface: have the same color characteristics as the upper surface.

Keeping quality: In the greenhouse, individual flowers remain aesthetically pleasing up to 6 days; in the home 8 to 13 days with room temperatures of 17° C. and high, natural light intensity.

Fragrance: There is little or no fragrance.

Reproductive organs:

*Androecium.*—Typical carnation except has aborted 9 to 21 filaments, aborted anthers and no pollen.

*Gynoecuim.*—Typical of carnation in all respects; pistil is 1.7 to 2.6 cm in length grooved and has 2 styles and stigmas. The stigmas are white and obtain a red tint at maturity.

Disease resistance: The plant has been found free of pathogen races currently associated with standard carnation cultivars, including the wilts and Etched Ring of Fleck viruses.

I claim:

1. A new and distinct cultivar of *Dianthus caryophyllus,* Linn, identified as 85-215-120A and known as Redcloud and substantially as herein described and illustrated.

* * * * *

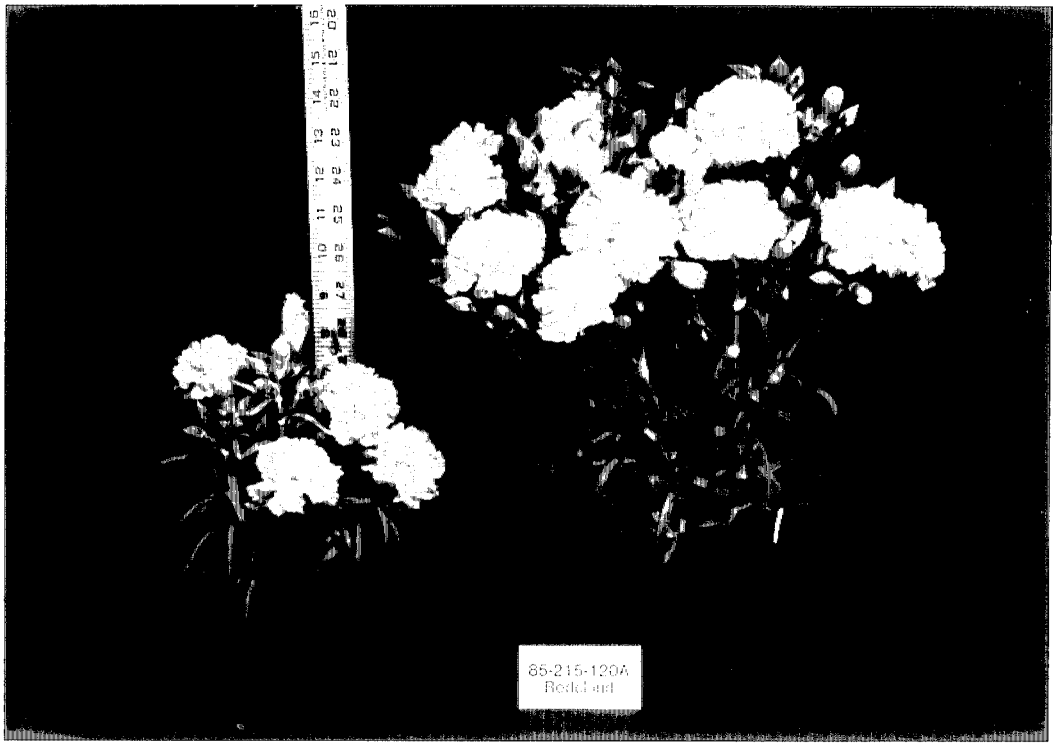
85-215-120A
Redcloud
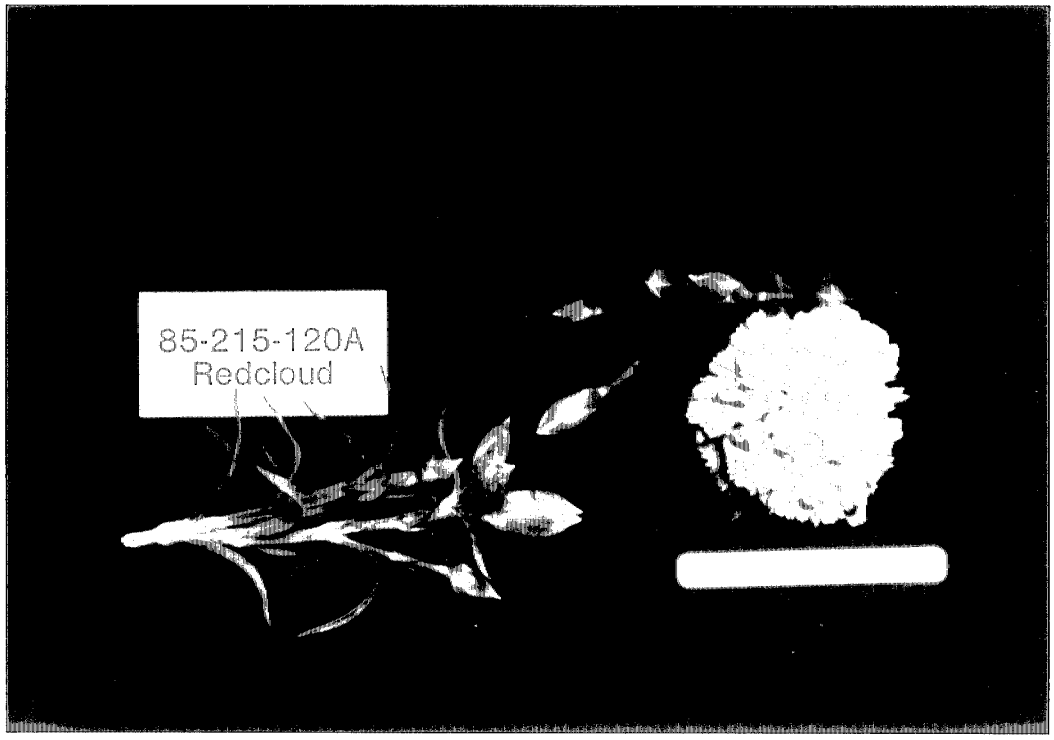
85-215-120A
Redcloud